(12) United States Patent
Italiaie et al.

(10) Patent No.: US 11,278,431 B2
(45) Date of Patent: Mar. 22, 2022

(54) SPINAL IMPLANT SYSTEM AND METHOD (71) Applicant: Warsaw Orthopedic, Inc., Warsaw, IN (US)

(72) Inventors: Christel Italiaie, Memphis, TN (US); Mark R. Grizzard, Munford, TN (US); Matthew T. Marrapode, Boulder, CO (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 290 days.

(21) Appl. No.: 16/383,742

(22) Filed: Apr. 15, 2019

(65) Prior Publication Data

US 2020/0323652 A1 Oct. 15, 2020

(51) Int. Cl.
*A61F 2/46* (2006.01)
*A61F 2/44* (2006.01)
*A61B 17/70* (2006.01)
*A61F 2/30* (2006.01)

(52) U.S. Cl.
CPC ............ *A61F 2/4611* (2013.01); *A61F 2/442* (2013.01); *A61B 17/7076* (2013.01); *A61F 2/30744* (2013.01); *A61F 2/4455* (2013.01); *A61F 2220/0025* (2013.01)

(58) Field of Classification Search
CPC ............ A61B 17/7032; A61B 17/7076; A61B 17/7085; A61B 17/7091; A61B 17/708; A61B 17/7083
See application file for complete search history.

(56) References Cited

U.S. PATENT DOCUMENTS

| 7,666,189 | B2 | 2/2010 | Gerber et al. | |
| 9,149,307 | B2* | 10/2015 | Sandstrom | A61B 17/7086 |
| 10,070,901 | B2* | 9/2018 | Sandstrom | A61B 17/7085 |
| 2011/0263945 | A1 | 10/2011 | Peterson et al. | |
| 2013/0096635 | A1 | 4/2013 | Wall et al. | |
| 2013/0245705 | A1* | 9/2013 | McBride | A61B 17/708 606/86 R |
| 2014/0100617 | A1* | 4/2014 | Sandstrom | A61B 17/7085 606/86 A |
| 2016/0113685 | A1 | 4/2016 | Ishii et al. | |

OTHER PUBLICATIONS

International Search Report and Written Opinion of the International Searching Authority, European Patent Office, PCT/US2019/056683, dated Feb. 4, 2020.

\* cited by examiner

*Primary Examiner* — Anu Ramana
(74) *Attorney, Agent, or Firm* — Sorell, Lenna & Schmidt, LLP (57) ABSTRACT

An implant support cap comprises a wall defining a cavity and at least one longitudinal passageway. The wall includes a guide engageable with an implant support member to orient the implant support member with the at least one passageway such that the implant support member is connectable with the wall. Systems, surgical instruments, spinal constructs, implants and methods are disclosed.

19 Claims, 6 Drawing Sheets

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as kyphosis, scoliosis and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, an implant support cap is provided. The implant support cap comprises a wall defining a cavity and at least one longitudinal passageway. The wall includes a guide engageable with an implant support member to orient the implant support member with the passageway such that the implant support member is connectable with the wall. In some embodiments, systems, surgical instruments, spinal constructs, implants and methods are disclosed.

In one embodiment, the implant support cap includes a wall defining a cavity and including mating grooves. The mating grooves define a first longitudinal passageway and a second longitudinal passageway. The wall includes an angled distal surface engageable with an implant support member including spaced apart extender tabs. The distal surface includes a first opening communicating with the first passageway and a second opening communicating with the second passageway to orient the tabs with the passageways such that the implant support member is connectable with the wall.

In one embodiment, a spinal implant system is provided. The spinal implant system comprises an implant support cap defining a cavity and including mating grooves defining a first longitudinal passageway and a second longitudinal passageway. The cap includes an angled distal surface having a first opening communicating with the first passageway and a second opening communicating with the second passageway. An implant support member includes spaced apart extender tabs engageable with the distal surface in a configuration to guide the tabs into the passageways such that the implant support member is connectable with the cap. An implant receiver is connected to the tabs.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument, such as, for example, an extender cap configured to guide and/or align one or more components of an implant support, implant and/or spinal construct into engagement for connection and/or assembly of the components. In some embodiments, the surgical instrument includes a guide to align the implant support, for example, at least one extender tab with at least one longitudinal passageway for connection with the extender cap. In some embodiments, the guide includes at least one opening disposed in communication with the at least one passageway to facilitate connection with the implant support. In some embodiments, the guide includes an angled surface configured to facilitate disposal of the extender tabs with the extender cap.

In some embodiments, the surgical instrument includes a guide engageable with at least one extender tab to guide and/or align the at least one extender tab into the at least one passageway, for example, axial slots. In some embodiments, the slots are configured to dispose the extender tabs with a cavity of the extender cap.

In some embodiments, the extender tabs are configured for aligning an implant, such as, for example, a bone fastener, with various instruments and providing an access path for set screws and rods. In some embodiments, the extender tabs are connectable with the bone fastener.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior."

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions of bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

Figure 1:
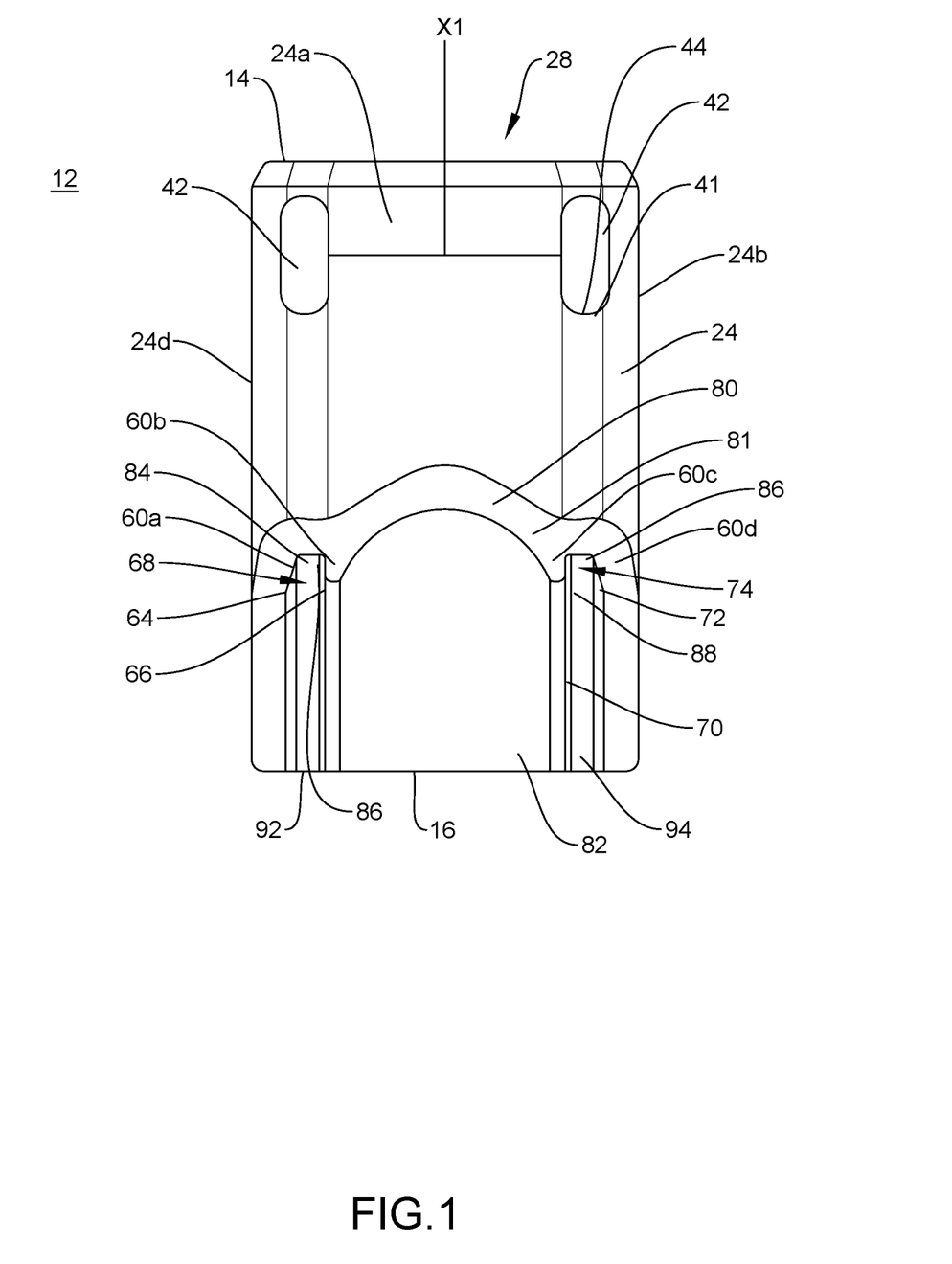
FIG. 1 is a side view of components of one embodiment of a surgical system in accordance with the principles of the present disclosure.
Figure 2:
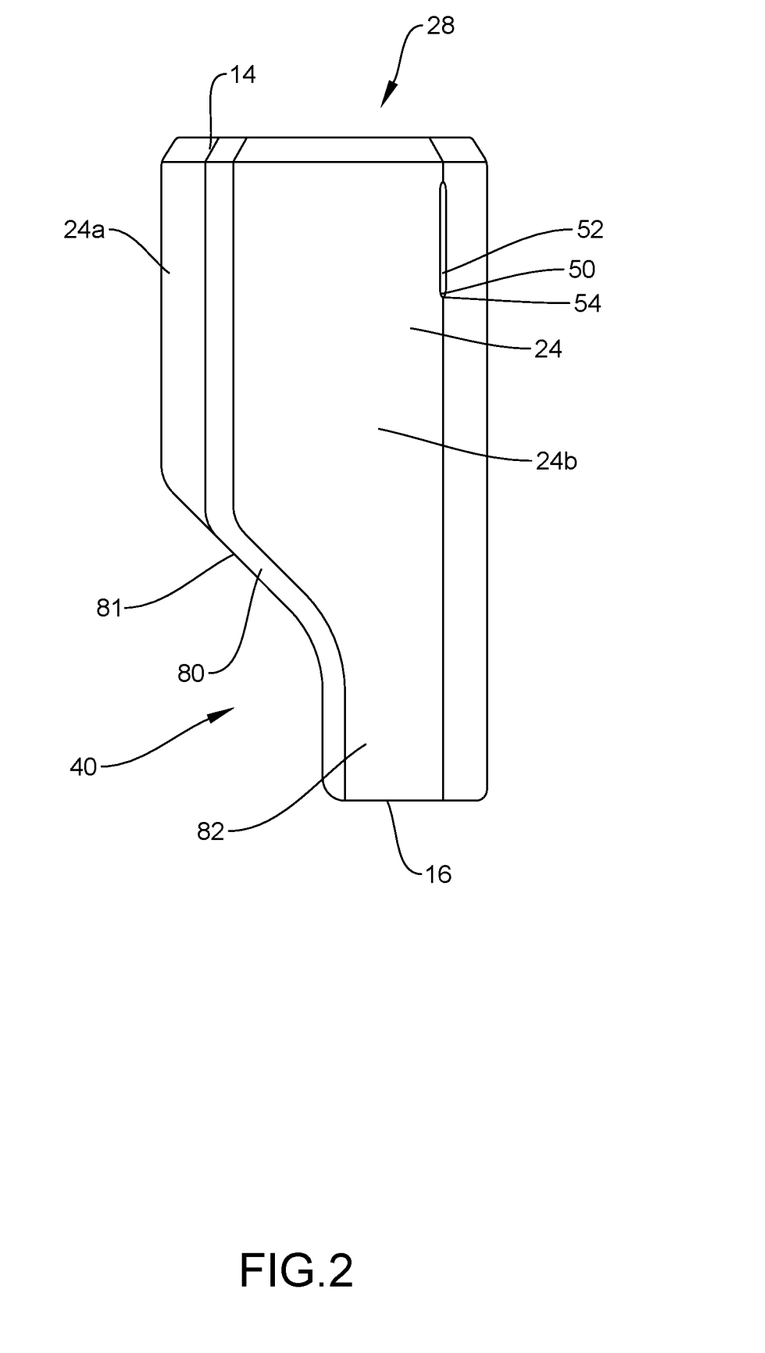
FIG. 2 is another side view of the components shown in FIG. 1.
Figure 3:
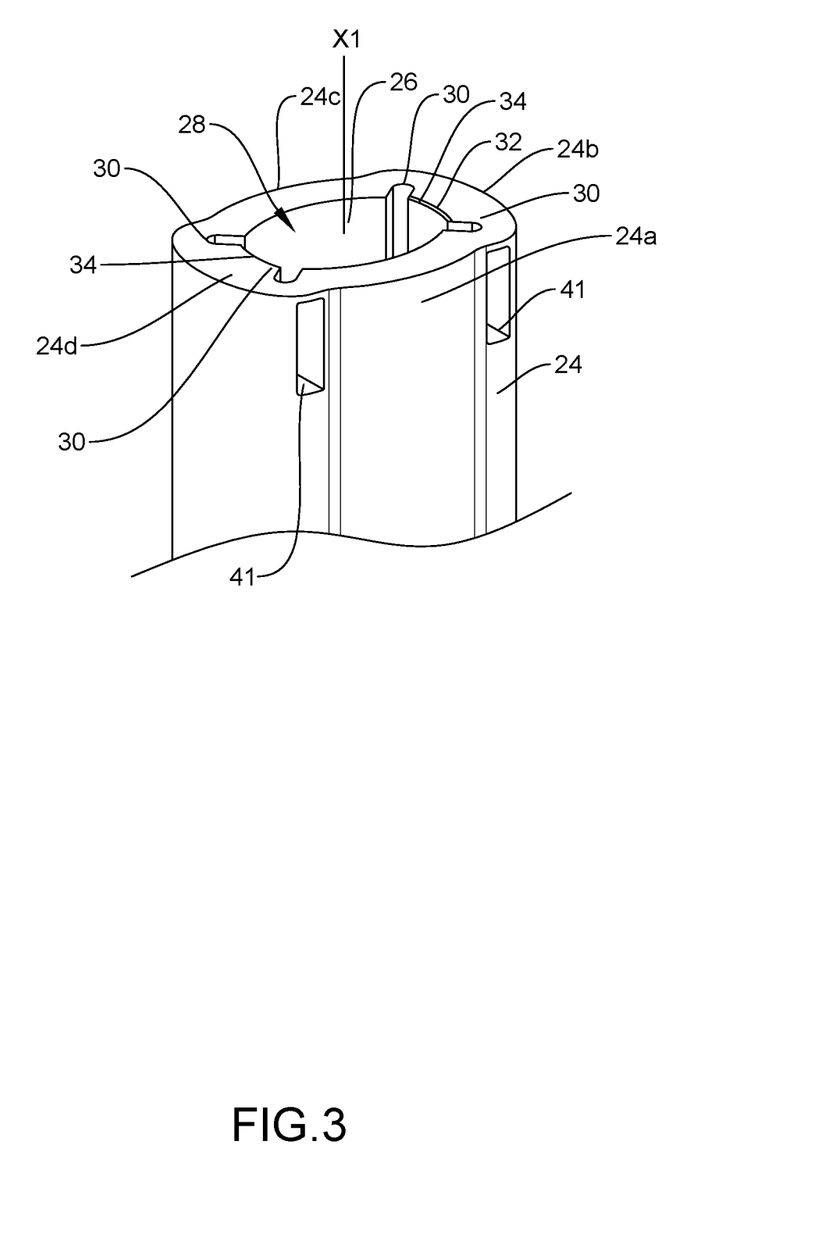
FIG. 3 is a break-away perspective view of the components shown in FIG. 1.
Figure 4:
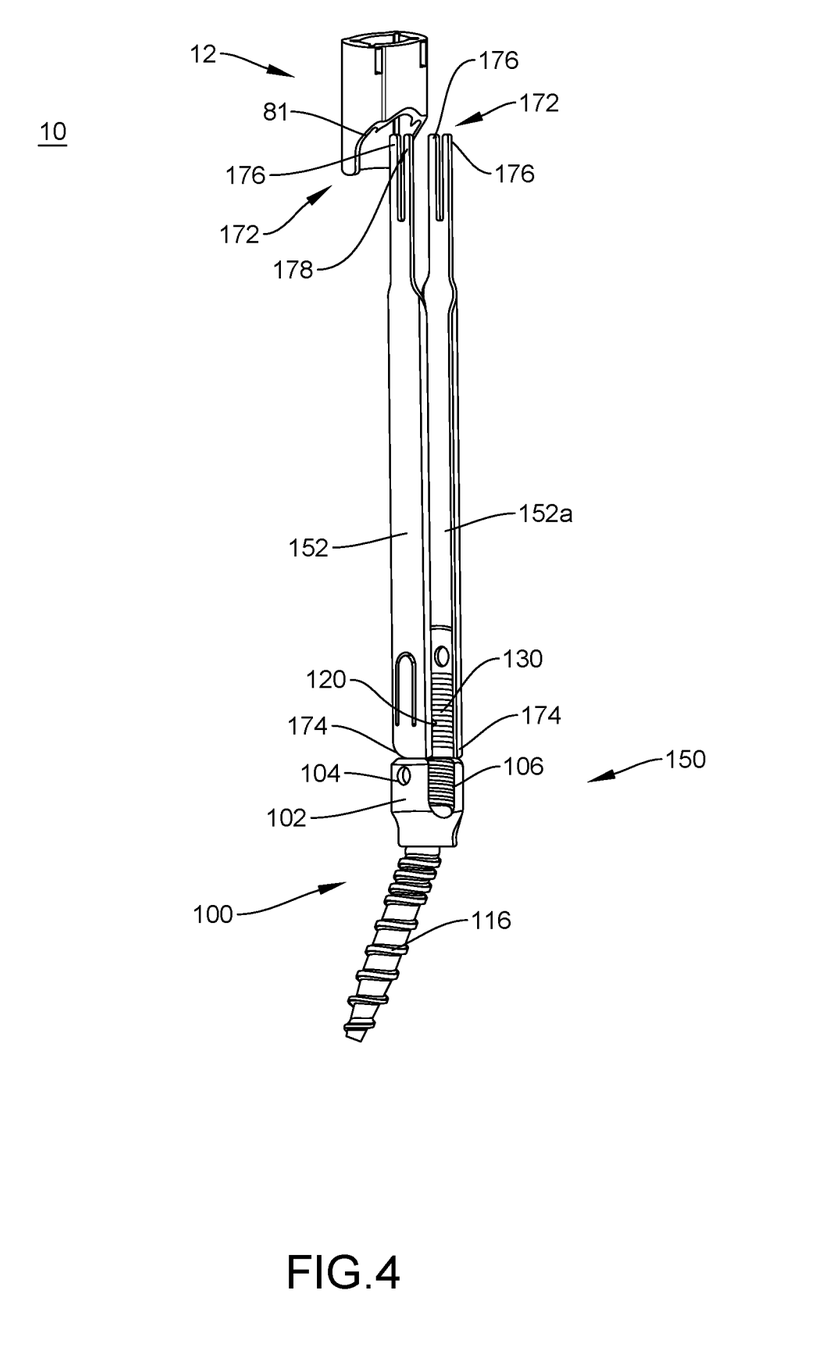
FIG. 4 is a perspective view of a first step of the assembly of the components of one embodiment of a surgical system in accordance with the principles of the present disclosure.
Figure 5:
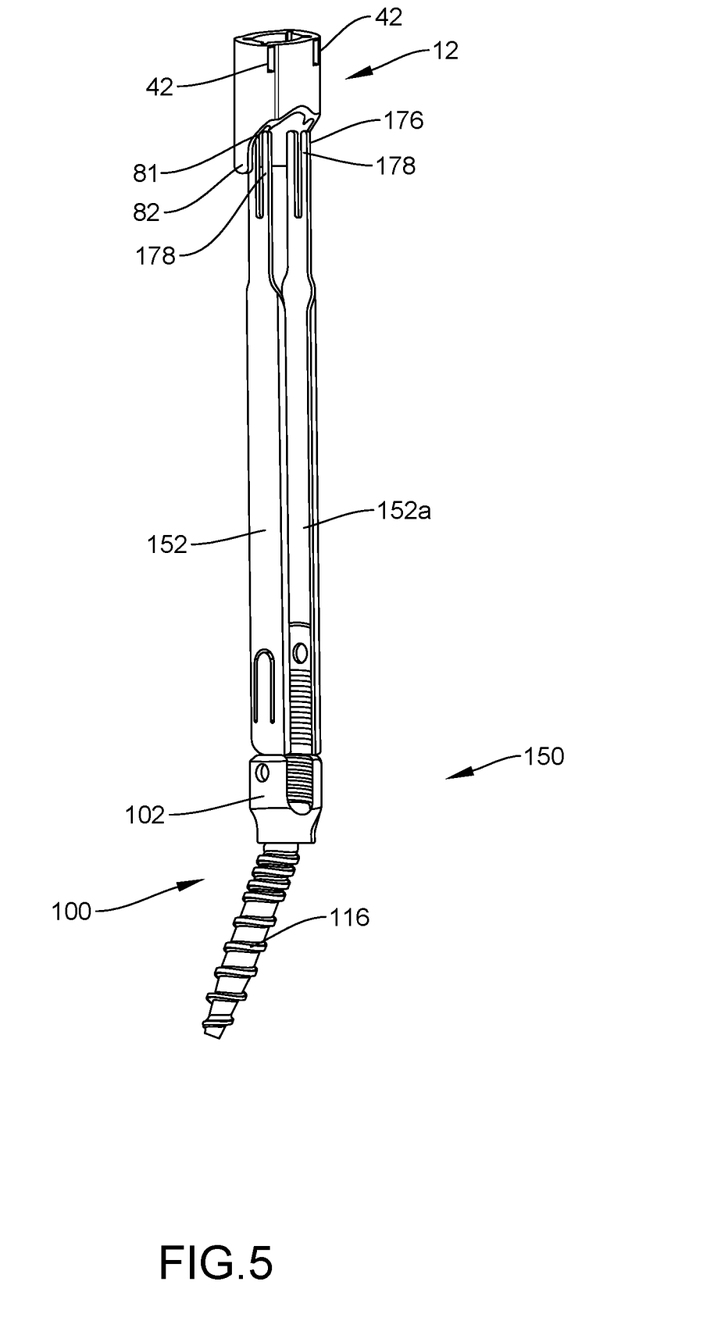
FIG. 5 is a perspective view of a second step of the assembly of the components of one embodiment of a surgical system in accordance with the principles of the present disclosure.
Figure 6:
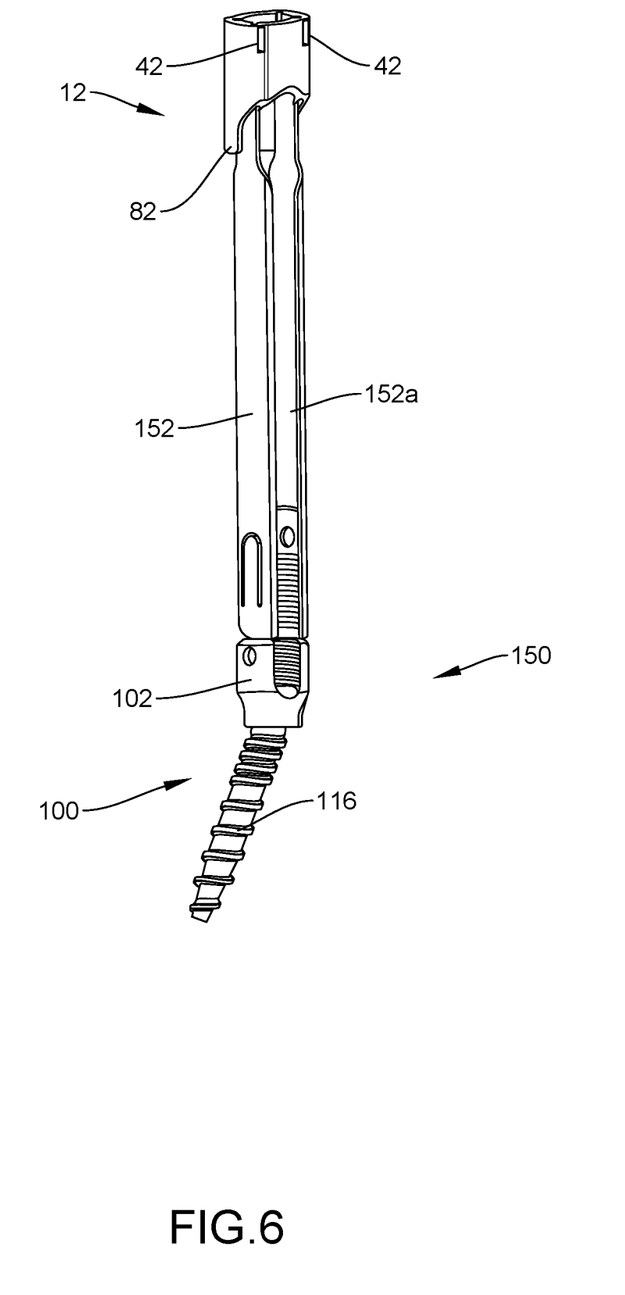
FIG. 6 is a perspective view of a third step of the assembly of the components of one embodiment of a surgical system in accordance with the principles of the present disclosure.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a surgical system, such as, for example, a spinal implant system 10. An embodiment of system 10 is shown in FIGS. 4-6. FIGS. 1-3 show a few components of the system.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency for imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 10 includes an implant support cap, for example, an extender cap 12. Cap 12 is configured to guide and/or align an implant support member, such as, for example, extender tabs 152, 152a into engagement with cap 12 for connection and/or assembly of the components of an extender connected to a bone fastener assembly 150. In some embodiments, cap 12 comprises a guide 40 configured to facilitate connection of extender tabs 152, 152a with cap 12.

Cap 12 extends between an end 14 and an end 16 defining an axis X1. Cap 12 includes a wall 24. Wall 24 includes portions 24a, 24b, 24c and 24d. Wall 24 includes an inner surface 26 extending along portions 24a, 24b, 24c and 24d. Surface 26 defines a cavity 28 configured for disposal of extender tabs 152, 152a. Cavity 28 includes a substantially rectangular configuration. In some embodiments, cavity 28 has various configurations including, for example, round, oval, polygonal, irregular, consistent, variable, uniform and non-uniform.

Portions 24a, 24b, 24c and 24d meet respectively at corners 30 along the inner surface of wall 24. In some embodiments, the inner surfaces of portions 24a, 24b, 24c and 24d include an arcuate, rounded, or partially rounded or arcuate, surface forming corners 30, as shown by way of example in FIG. 3. In some embodiments, corners 30 may have various configurations including, for example, irregular, consistent, variable, uniform and non-uniform. Corners 30 extend axially along wall 24. In some embodiments, corners 30 extend at alternate orientations along wall 24, such as, for example, at transverse, perpendicular and/or other angular orientations such as acute or obtuse, and/or may be offset or staggered, with respect to axis X1.

A projection 34 is disposed with portions 24b, 24d, as shown in FIG. 3. Projection 34 is configured to abut extender tabs 152, 152a to retain extender tabs 152, 152a within cavity 28. For example, as extender tabs 152, 152a translate into engagement with cap 12, projection 34 resists and/or prevents extender tabs 152, 152a from passing through cavity 28 during insertion.

Portion 24a includes a surface 41 connectable with a portion of extender tabs 152, 152a, such as, for example, a spring tip 178 or a spring tip 176, as described herein. Surface 41 defines at least one groove, such as, for example, a pocket 42, as shown in FIG. 1. Portion 24a includes a pair of pockets 42. Pockets 42 are configured for a mating engagement with spring tips 178, as described herein. Surface 41 is configured as a lock 44 to resist and/or prevent disengagement of spring tips 178 from pocket 42, as described herein.

Portion 24c includes a surface 50, similar to surface 41, connectable with a portion of extender tabs 152, 152a, such as, for example, spring tip 178 or spring tip 176, as described herein. Surface 50 defines at least one groove, such as, for example, a pocket 52, as shown in FIG. 2. Portion 24c includes a pair of pockets 52, as shown in FIG. 2. Pockets 52 are configured for a mating engagement with spring tips 176, as described herein. Pockets 52 are disposed in alignment with pockets 42, as shown in FIG. 1, to facilitate engagement of spring tips 176. Surface 50 is configured as a lock 54 to resist and/or prevent disengagement of spring tips 176 from pocket 52, as described herein.

Pockets 42, 52 are configured for engagement with spring tips 176, 178, as shown in FIG. 6. Disposal of spring tips 176, 178 with pockets 42, 52 is configured to resist and/or prevent extender tabs 152, 152a from disengaging from cap 12. In some embodiments, pockets 42, 52 are disposed parallel to axis X1. In some embodiments, pockets 42, 52 are disposed at alternate orientations relative to axis a, such as, for example, at transverse, perpendicular and/or other angular orientations such as acute or obtuse, and/or may be offset or staggered. In some embodiments, locks 44, 54 are configured to provide audible and/or tactile indicia, such as, for example, an audible click indicating engagement of spring tips 176, 178 with cap 12.

Wall 24 includes longitudinal rails 60a, 60b, 60c and 60d extending along axis X1. Rail 60a includes surface 64. Rail 60b includes a surface 66. Surfaces 64, 66 define a passageway, such as, for example, an axial slot 68. Slot 68 extends along axis X1. Slot 68 is configured to facilitate engagement of extender tab 152 with cap 12, as described herein. In some embodiments, all or only a portion of surfaces 64, 66 may have alternate configurations, such as, for example, irregular, uniform, non-uniform, offset, staggered, tapered, arcuate or undulating. Surfaces 64, 66 direct and/or guide insertion of extender tab 152 into cavity 28.

Rail 60c includes surface 70. Rail 60d includes a surface 72. Surfaces 70, 72 define a passageway, such as, for example, an axial slot 74. Slot 74 extends along axis X1. Slot 74 is configured to facilitate engagement of extender tab 152a with cap 12, as described herein. In some embodiments, all or only a portion of surfaces 70, 72 may have alternate configurations, such as, for example, irregular, uniform, non-uniform, offset, staggered, tapered, arcuate or undulating. Surfaces 70, 72 direct and/or guide insertion of extender tab 152a into cavity 28.

Extender tabs 152, 152a are configured to slide and/or translate along slots 68, 74 to position extender tabs 152, 152a within cavity 28 and into locking engagement with cap 12, as described herein. Slots 68, 74 are configured to splay extender tabs 152, 152a to facilitate engagement of spring tips 176, 178 with pockets 42, 52.

Guide 40 is configured to guide and/or direct extender tabs 152, 152a into cavity 28. Guide 40 includes a distal surface 80 of wall 24 and an extension 82 extending from portion 24c, as shown in FIG. 2. Surface 80 includes an opening 84 disposed in communication with slot 68. Surface 80 includes an opening 86 disposed in communication with slot 74. Surface 80 is configured to guide and/or direct extender tabs 152, 152a into slots 68, 74.

Surface 80 is disposed at an angle relative to axis X1 such that surface 80 is disposed in a transverse orientation relative to slots 68, 74 to define a ramp 81, as shown in FIGS. 2 and 3. Ramp 81 is selectively inclined to facilitate translation and/or guiding of extender tabs 152, 152a into slots 92, 94 and/or slots 68, 74. In some embodiments, surface 80 is disposed at alternate orientations relative to axis X1, such as, for example, at transverse, perpendicular and/or other angular orientations such as acute or obtuse, and/or may be offset or staggered. In some embodiments, surface 80 is selectively inclined to facilitate translation and/or disengagement of extender tabs 152, 152a from cap 12.

Extension 82 includes a slot 92 and a slot 94. Slot 90 is disposed coaxially with slot 68, as shown in FIG. 1. Slot 92 is disposed coaxially with slot 74. Extender tabs 152, 152a are guided, directed and/or aligned via slidable translation along slots 90, 92 into slots 68, 74. This configuration facilitates alignment of extender tabs 152, 152a for assembly with cap 12.

Bone fastener assembly 150 includes a bone fastener 100. Bone fastener 100 includes a receiver 102. Receiver 102 is connected to extender tabs 152, 152a that extend along axis X1. Receiver 102 includes a pair of spaced apart arms 104, 106 that define an implant cavity configured for disposal of a component of a spinal construct, such as, for example, a spinal rod (not shown). Receiver 102 includes a socket configured for engagement with a surgical instrument. Receiver 102 includes an inner surface having a thread form located adjacent arm 104 and a thread form located adjacent arm 106. The thread forms of arms 104, 106 are configured for engagement with a coupling member. Bone fastener 100 includes a threaded shaft 116. Shaft 116 is configured to penetrate tissue, such as, for example, bone.

Arm 104 includes a break away tab 120 that is frangibly connected to arm 104 such that manipulation of tab 120 relative to arm 104 can fracture and separate tab 120 from arm 104 at a predetermined force and/or torque limit, as described herein. Arm 106 includes a break away tab 130 that is frangibly connected to arm 106 such that manipulation of tab 130 relative to arm 106 can fracture and separate tab 130 from arm 106 at a predetermined force and/or torque limit, as described herein. In some embodiments, as force and/or torque is applied to tabs 120, 130 and resistance increases, for example, the predetermined torque and force limit is approached.

In some embodiments, tabs 120, 130 can fracture and separate at a predetermined force or torque limit, which may be in a range of approximately 2 Newton meters (N-m) to approximately 8 N-m. In some embodiments, tabs 120, 130 and arms 104, 106 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 120, 130.

Bone fastener assembly 150 includes extender tabs 152, 152a connected to bone fastener 100. Extender tabs 152, 152a extend between a proximal end 172 and a distal end 174. Proximal end 172 includes spring tips 176, 178, as shown in FIG. 4. Spring tips 176, 178 are interchangeably attachable with pockets 42, 52 of cap 12 to resist and/or prevent disengagement of spring tips 176, 178, as described herein. Distal ends 174 are configured for slidable disposal of a portion of bone fastener 100, such as, for example, tabs 120, 130. In some embodiments, tabs 120, 130 are configured to releasably fix extender tabs 152, 152a with bone fastener 100.

In assembly, operation and use, spinal implant system 10, similar to the systems and methods described herein, is employed with a surgical procedure, such as, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In use, to treat vertebrae (not shown), a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of the vertebrae as well as for aspiration and irrigation of a surgical region.

Pilot holes (not shown) are made in selected levels of vertebrae for receiving shafts 116 of bone fastener assemblies 150. A surgical instrument, such as, for example, a driver is connected to bone fastener 100 and bone fasteners 100 are engaged with vertebrae. Extender tabs 152, 152a are connected to bone fasteners 100, as described herein.

Extender tabs 152, 152a are positioned adjacent cap 12, as shown in FIG. 4. Extender tabs 152, 152a are aligned with guide 40 such that ramp 81 directs extender tabs 152, 152a into slots 92, 94 of extension 82. Extender tabs 152, 152a slide and/or translate along slots 92, 94. Slots 92, 94 direct and/or align extender tabs 152, 152a through openings 84, 86 into slots 68, 74.

In some embodiments, extender tabs 152, 152a are positioned with slots 92, 94 of extension 82 such that extender tabs 152, 152a slide and/or translate along slots 92, 94. Slots 92, 94 direct and/or align extender tabs 152, 152a through openings 84, 86 for disposal into slots 68, 74. Ramp 81 facilitates directing and/or aligning extender tabs 152, 152a into slots 92, 94 of extension 82.

Surfaces 64, 66 of slot 68 and surfaces 70, 72 of slot 74 are configured to cause extender tabs 152, 152a to splay for disposal with pockets 42, 52, as shown in FIG. 6. In some embodiments, spring tips 176,178 engage surfaces 44, 54 and audible and/or tactile indicia, such as, for example, a click indicates engagement of spring tips 176, 178 with cap 12. Projection 34 resists and/or prevents disengagement of cap 12 from cavity 28 during insertion of extender tabs 152, 152a.

In some embodiments, the surgical procedure includes delivering a spinal rod along the surgical pathway for connection with one or more bone fasteners 100. A reduction instrument (not shown) engages the spinal rod for reduction with receivers 102 and fixed thereto. In some embodiments, a tab breaker is engaged with extender tabs 152, 152a and is manipulated to apply a force to extender tabs 152, 152a and/or tabs 120, 130. As the force applied reaches a selected torque limit, the tab breaker breaks off extender tabs 152, 152a and/or tabs 120, 130 from bone fasteners 100.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An implant support cap comprising:
a body having a longitudinal axis and defining a cavity; and an extension extending from a distal end of the body, the extension comprising a first longitudinal passageway and a second longitudinal passageway, the cavity extending along the longitudinal axis, the cap being engageable with an implant support member to orient the implant support member with the passageways such that the implant support member is connectable with the cap, the body including a pair of first openings and a pair of second openings, one of the first openings communicating with the first passageway, one of the second openings communicating with the second passageway the first openings being aligned along a first transverse axis, the second openings being aligned along a second transverse axis, the transverse axes extending perpendicular to the longitudinal axis, the body including a lock engageable with the implant support member.

2. An implant support cap as recited in claim 1, wherein: the body includes a distal surface, the distal surface communicating with the passageways.

3. An implant support cap as recited in claim 2, wherein: the distal surface is disposed in a transverse orientation relative to the longitudinal axis.

4. An implant support cap as recited in claim 1, wherein: the body includes an inner surface defining the cavity and an opposite outer surface, the openings each extending through the inner and outer surfaces.

5. An implant support cap as recited in claim 1, wherein: the body includes opposing first and second walls and opposing third and fourth walls each extending from the first wall to the second wall, the extension extending distally from the first wall such that the extension is spaced apart from the second wall.

6. An implant support cap as recited in claim 1, wherein: the body includes opposing first and second walls and opposing third and fourth walls each extending from the first wall to the second wall, the extension extending distally from the first, third and fourth walls such that the extension is spaced apart from the second wall.

7. An implant support cap as recited in claim 1, wherein: the extension includes mating grooves defining the passageways.

8. An implant support cap as recited in claim 7, wherein: the mating grooves define pocket surfaces engageable with proximal spring tips of the implant support member.

9. An implant support cap as recited in claim 1, wherein: the cap and the implant support member are engageable in a snap-fit assembly.

10. An implant support cap as recited in claim 1, wherein: the lock is releasably engageable with the implant support member.

11. An implant support cap as recited in claim 1, wherein: the body includes a flange oriented to abut the implant support member.

12. An implant support cap as recited in claim 1, wherein: the body includes at least one corner.

13. An implant support cap as recited in claim 1, wherein: the second passageway is spaced apart from the first passageway.

14. An implant support cap as recited in claim 13, wherein:
the extension includes a plurality of longitudinal rails defining the passageways.

15. An implant support cap comprising:
a body having a longitudinal axis and defining a cavity, the cavity a extending along the longitudinal axis; and
an extension extending from a distal end of the body, the extension including mating grooves, the mating grooves defining a first longitudinal passageway and a second longitudinal passageway, the distal end including an angled distal surface engageable with an implant support member including spaced apart extender tabs, the body including a pair of first openings and a pair of second openings, one of the first openings communicating with the first passageway, one of the second openings communicating with the second passageway, the first openings being aligned along a first transverse axis, the second openings being aligned along a second transverse axis, the transverse axes extending perpendicular to the longitudinal axis.

16. An implant support cap as recited in claim 15, wherein:
the openings each have an oblong configuration cross-sectional shape.

17. An implant support cap as recited in claim 15, wherein:
the cap and the tabs are engageable in a snap-fit assembly.

18. An implant support cap as recited in claim 15, wherein:
the body includes a lock, the lock being releasably engageable with the tabs.

19. A spinal implant system comprising:
an implant support cap comprising:
a body having a longitudinal axis and defining a cavity, the cavity a extending along the longitudinal axis, and
an extension extending from a distal end of the body, the extension including mating grooves defining a first longitudinal passageway and a second longitudinal passageway, the extension including a pair of first openings and a pair of second openings, one of the first openings communicating with the first passageway, one of the second openings communicating with the second passageway, the first openings being aligned along a first transverse axis, the second openings being aligned along a second transverse axis, the transverse axes extending perpendicular to the longitudinal axis;

an implant support member including spaced apart extender tabs configured for disposal in the passageways and the openings such that the implant support member is connectable with the cap; and an implant receiver connected to the tabs.

* * * * *